(12) United States Patent
Jennings

(10) Patent No.: US 7,144,739 B2
(45) Date of Patent: Dec. 5, 2006

(54) PRESSURE MEASUREMENT AND RELIEF FOR MICROWAVE-ASSISTED CHEMICAL REACTIONS

(75) Inventor: William E. Jennings, Wingate, NC (US)

(73) Assignee: CEM Corporation, Charlotte, NC (US)

( * ) Notice: Subject to any disclaimer, the term of this patent is extended or adjusted under 35 U.S.C. 154(b) by 456 days.

(21) Appl. No.: 10/065,851

(22) Filed: Nov. 26, 2002

(65) Prior Publication Data

US 2004/0101441 A1    May 27, 2004

(51) Int. Cl.
*G01N 7/16* (2006.01)
*H05B 6/64* (2006.01)
*G05D 16/06* (2006.01)

(52) U.S. Cl. ............... 436/148; 215/234; 215/247; 215/271; 215/317; 219/678; 219/679; 219/685; 219/756; 422/82.13; 422/102; 422/105; 422/112; 422/117; 422/119

(58) Field of Classification Search ............. 422/82.13, 422/102, 105, 112, 117, 119; 436/148, 155; 219/756, 678–679, 685; 73/726–727; 215/234, 215/247, 271, 317–318
See application file for complete search history.

(56) References Cited

U.S. PATENT DOCUMENTS

| | | | |
|---|---|---|---|
| 2,612,596 A | 9/1952 | Gross | |
| 2,704,802 A | 3/1955 | Blass | |
| 3,210,511 A | 10/1965 | Smith | |
| 3,377,564 A | 4/1968 | Stecca | |
| 3,573,680 A | 4/1971 | Carignan | |
| 3,810,248 A | 5/1974 | Risman | |
| 3,823,295 A | 7/1974 | Simon | |
| 3,843,862 A | 10/1974 | Staats | |
| 3,851,271 A | 11/1974 | Cooke | |
| 3,855,440 A | 12/1974 | Staats | |
| 3,907,144 A * | 9/1975 | Winkler | .................. 215/47 |
| 3,927,347 A | 12/1975 | Farney | |
| 4,019,009 A | 4/1977 | Kusunoki | |
| 4,028,651 A | 6/1977 | Leetmaa | |
| 4,065,654 A | 12/1977 | Moore | |
| 4,094,641 A * | 6/1978 | Friswell | .................. 436/180 |
| 4,133,997 A | 1/1979 | Thuleen | |
| 4,251,787 A | 2/1981 | Young | |

(Continued)

FOREIGN PATENT DOCUMENTS

DE    3919601    * 12/1989

(Continued)

OTHER PUBLICATIONS

Baghurst, D. R. et al, Journal of the Chemical Society, Dalton Transactions 1992, 1151-1155.*

(Continued)

*Primary Examiner*—Arlen Soderquist
(74) *Attorney, Agent, or Firm*—Summa, Allan & Additon, P.A.

(57) ABSTRACT

A pressure-sealing, pressure-monitoring closure for non-invasively sealing a reaction vessel to a defined release pressure in microwave-assisted chemistry is disclosed. The closure includes a pressure-resistant, microwave-transparent reaction vessel, one portion of which defines a mouth, a flexible pressure-transmitting releasable cover assembly on the mouth of the vessel, a pressure transducer on the cover and external to the vessel for monitoring the pressure in the vessel as exerted against the flexible cover, and a clamp for urging the vessel, the cover and the transducer together under a defined force so that when the pressure in the vessel exceeds the defined force, the cover can flex and release the pressure from the vessel.

40 Claims, 6 Drawing Sheets

U.S. PATENT DOCUMENTS

| | | | |
|---|---|---|---|
| 4,347,216 A * | 8/1982 | Kawasaki et al. | 422/78 |
| 4,354,083 A | 10/1982 | Staats | |
| 4,410,865 A | 10/1983 | Young | |
| 4,458,126 A | 7/1984 | Dills | |
| 4,490,597 A * | 12/1984 | Mengel | 219/735 |
| 4,518,932 A | 5/1985 | Pickering | |
| 4,670,404 A | 6/1987 | Swift | |
| 4,672,996 A * | 6/1987 | Floyd et al. | 137/522 |
| 4,673,894 A | 6/1987 | Rogers | |
| 4,677,403 A | 6/1987 | Kich | |
| 4,681,740 A | 7/1987 | Commarmot | 422/78 |
| 4,693,867 A | 9/1987 | Commarmot | |
| 4,700,146 A | 10/1987 | Barton | |
| 4,736,083 A * | 4/1988 | Saville | 219/686 |
| 4,770,906 A * | 9/1988 | Harwell et al. | 427/212 |
| 4,851,631 A | 7/1989 | Wendt | |
| 4,877,624 A * | 10/1989 | Floyd et al. | 426/241 |
| 4,882,128 A | 11/1989 | Hukvari | |
| 4,904,450 A | 2/1990 | Floyd | |
| 4,933,529 A * | 6/1990 | Saville | 219/686 |
| 4,965,540 A | 10/1990 | Sullivan | |
| 5,015,445 A * | 5/1991 | Doleman et al. | 422/104 |
| 5,059,400 A | 10/1991 | Benezech | 422/186 |
| 5,088,612 A * | 2/1992 | Storar et al. | 215/247 |
| 5,191,182 A | 3/1993 | Gelorme | |
| 5,204,065 A | 4/1993 | Floyd | |
| 5,206,479 A * | 4/1993 | Zakaria et al. | 219/754 |
| 5,230,865 A | 7/1993 | Hargett | |
| 5,246,674 A | 9/1993 | Katschnig | |
| 5,264,185 A | 11/1993 | Floyd | |
| 5,270,010 A * | 12/1993 | Lautenschlager | 422/102 |
| 5,294,895 A | 3/1994 | Feeney | |
| 5,303,835 A * | 4/1994 | Haber et al. | 215/247 |
| 5,304,766 A | 4/1994 | Baudet | |
| 5,308,944 A | 5/1994 | Stone-Elander | 219/687 |
| 5,320,804 A | 6/1994 | Zakaria | |
| 5,344,493 A | 9/1994 | Jackson | |
| 5,369,034 A | 11/1994 | Hargett | |
| 5,382,414 A * | 1/1995 | Lautenschlager | 422/186 |
| 5,407,641 A | 4/1995 | Katschnig | |
| 5,418,510 A | 5/1995 | Gray | |
| 5,420,401 A | 5/1995 | Jacquault | |
| 5,426,402 A | 6/1995 | Mariani | |
| 5,427,741 A * | 6/1995 | Bennett | 422/102 |
| 5,447,077 A * | 9/1995 | Lautenschlager | 73/863.11 |
| 5,481,233 A | 1/1996 | Manolache | |
| 5,601,745 A * | 2/1997 | Schalk et al. | 219/710 |
| 5,637,803 A * | 6/1997 | Schalk et al. | 73/744 |
| 5,647,939 A * | 7/1997 | Gee et al. | 156/272.6 |
| 5,659,874 A | 8/1997 | Rault | 422/186 |
| 5,672,316 A | 9/1997 | Knapp | |
| 5,691,677 A | 11/1997 | De Maron | |
| 5,725,835 A | 3/1998 | Lautenschlager | |
| 5,731,750 A | 3/1998 | Tatomir | |
| 5,777,534 A | 7/1998 | Harrison | |
| 5,796,080 A | 8/1998 | Jennings | |
| 5,919,711 A * | 7/1999 | Boyd et al. | 436/178 |
| 5,932,075 A | 8/1999 | Strauss | |
| 5,981,924 A | 11/1999 | Lautenschlager | |
| 5,986,526 A | 11/1999 | Kopal | |
| 5,998,774 A | 12/1999 | Joines | |
| 6,011,247 A | 1/2000 | Grillo et al. | |
| 6,057,645 A | 5/2000 | Srivastava | |
| 6,084,226 A | 7/2000 | Greene | |
| 6,086,826 A | 7/2000 | Thomas | |
| 6,092,924 A | 7/2000 | Scalese | |
| 6,097,263 A | 8/2000 | Mueller | |
| 6,136,276 A * | 10/2000 | Hargett et al. | 422/102 |
| 6,227,041 B1 | 5/2001 | Collins | |
| 6,258,329 B1 * | 7/2001 | Mutterer et al. | 422/186.29 |
| 6,268,570 B1 | 7/2001 | McLendon | |
| 6,287,526 B1 | 9/2001 | Hargett, Jr. | 422/242 |
| 6,288,379 B1 | 9/2001 | Greene | |
| 6,302,577 B1 | 10/2001 | Jennings | |
| 6,320,170 B1 | 11/2001 | Jennings | |
| 2002/0101310 A1 | 8/2002 | Jennings | 333/248 |
| 2002/0102738 A1 | 8/2002 | Jennings | 436/155 |
| 2002/0117498 A1 | 8/2002 | Jennings | 219/686 |
| 2002/0121513 A1 | 9/2002 | Jennings | 219/679 |

FOREIGN PATENT DOCUMENTS

| | | |
|---|---|---|
| DE | 19710499 | * 10/1997 |
| DE | 10016962 | * 10/2001 |
| JP | 05 345982 A | 12/1993 |
| JP | 6-96856 | 4/1994 |
| JP | 11 243000 A | 12/1999 |
| WO | WO02/062104 A2 | 8/2002 |

OTHER PUBLICATIONS

Zischka, M. et al, Fresenius' Journal of Analytical Chemistry 1998, 361, 90-95.*

Baasner, J. et al, Spectroscopy 1999, 14, 42-44.*

Matusiewicz, H. Analytical Chemistry 1999, 71, 3145-3149.*

Raner, Kevin D. et al.; *A New Microwave Reactor for Batchwise Organic Synthesis*; The Journal of Organic Chemistry, American Chemical Society, Easton, U.S.; vol. 60, No. 8, pp. 2456-2460.

* cited by examiner

PRESSURE MEASUREMENT AND RELIEF FOR MICROWAVE-ASSISTED CHEMICAL REACTIONS

BACKGROUND OF INVENTION

The present invention relates to microwave assisted chemical techniques. In particular, it relates to methods and apparatus for carrying out sophisticated chemical reactions, particularly organic synthesis and related types of reactions, with an emphasis on carrying out reactions rapidly in relatively small quantities to thereby more quickly evaluate larger numbers of reactants, products, by-products and chemical pathways.

The use of microwaves to provide the heat or the kinetic energy (or both) to drive certain types of chemical reactions is generally well understood. Microwaves are those waves within the portion of the electromagnetic spectrum with frequencies of between about 300 and 300,000 megahertz (MHz) and wavelengths of between about 1 centimeter and 1 meter. The borders between various types of electromagnetic radiation (e.g., visible, infrared, ultraviolet, etc.) are, however, arbitrary rather than definite. The terms are, however, well understood in their context and in this art.

Microwave radiation and microwave-assisted techniques are generally well-established for robust chemical reactions such as digestion and drying of suitable materials. More recently, the speed with which microwaves can apply energy to a reaction, and the fact that the microwave energy itself can drive the reaction rather than just creating heat to secondarily drive the reaction, has led to increased interest in using microwave radiation for more sophisticated chemical techniques, such as organic synthesis, particularly synthesis in relatively small quantities that are consistent with the needs of modern synthesis protocols, such as combinatorial chemistry. Both general and specific discussion of such techniques are set forth in Hayes, Microwave Synthesis-Chemistry at the Speed of Light, CEM Publishing (2002) (ISBN 0-9722229-0-1).

Accordingly, a new generation of instruments has been developed for this purpose, and by way of illustration and background, can be well understood by evaluating the disclosures of several co-pending and commonly assigned applications. These include published applications U.S. Pat. No. 20,020,101,310, U.S. Pat. No. 20,020,121,513, U.S. Pat. No. 20,020,117,498, U.S. Pat. No. 20,020,102,738 and WO 02/062104, and unpublished (to date) U.S. applications Ser. Nos. 09/773,898 filed Jan. 31, 2001 ("Pressure Measurement in Microwave-Assisted Chemical Synthesis") and 10/126,838, filed Apr. 19, 2002 ("Microwave Assisted Chemical Synthesis Instrument with Controlled Pressure Release"). The contents of all of these are incorporated entirely herein by reference.

As set forth in these disclosures, more recent techniques and instruments incorporate relatively small microwave cavities that support a single or other defined modes of microwave radiation that are more suitable for promoting reactions between reactants present in very small quantities that would be difficult to heat with more conventional microwave instruments. Commercially, recently available devices include the EXPLORER™, and DISCOVER™ instruments from CEM Corporation, the assignee of the present invention. In these instruments, a single mode cavity is matched with a removable attenuator, which also serves as a support mechanism for a reaction vessel. In this manner, reaction vessels can be quickly inserted into the instrument, have microwave radiation applied to them, and then be removed for the next step in whatever analysis or synthesis of interest is taking place.

As set forth in Publication No. U.S. Pat. No. 20,020,121,513, the pressure inside of a vessel during the application of microwaves can be measured by penetrating the vessel with a needle in communication with a pressure measuring device. In the "513 Publication, the reaction vessel is typically capped with a flexible, penetrable cover or septum through which a needle can be inserted without compromising the pressure integrity of the vessel, because of the manner in which the penetrable septum quickly surrounds and grips the penetrating needle. The annulus of the needle is in communication with a pressure-measuring device, typically a transducer, so that the pressure in the reaction can be monitored.

Although these instruments and the needle-penetrated septum arrangement for pressure measurement offer a number of advantages, there are additional types of reactions for which a physically-penetrating pressure measurement is less suitable.

For example, a pressure release may not be controllable; i.e., it may operate in an all-or-nothing fashion. Additionally, the contents of the vessel and the needle may be mutually reactive; i.e., the needle may corrode, react to form unwanted byproducts, or even catalyze an undesired or unexpected reaction. As another potential factor, certain reactions are most suitably carried out in the absence of oxygen (and thus in the absence of air) or, stated in the affirmative, in the presence of some inert gas such as nitrogen or one of the noble gases such as argon or helium. In such cases, pressure measurement using a device that penetrates into the reaction vessel and provides a communication path for fluids and gases outside of the vessel can be disadvantageous or inappropriate. Thus, in such cases it can be likewise disadvantageous to attempt to measure pressure using some sort of fluid communicating device, such as the needle, between the transducer and the vessel's contents.

Pressure measurement is, however, often an important factor in tracking the progress of certain reactions. The measured pressure can be an indication of desired products, undesired by-products, completion of a reaction, or loss of control over the reaction. Thus, resolving pressure-measurement problems by simply foregoing pressure measurement is an undesired option in many circumstances.

Accordingly, a need exists for a method of measuring pressure in such reaction vessels without penetrating the vessel during the reaction. Devices exist for such purposes, including (in a somewhat unrelated environment) U.S. Pat. No. 6,287,526, which is commonly assigned with the present application. In a more analogist environment, Personal Chemistry, Inc. (Foxboro, Mass.) provides the Emrys™ Synthesizer and Emrys™ Process Vials for this purpose.

The Emrys™ vessels nevertheless demonstrate certain of the problems with such vessels. As illustrated by Personal Chemistry (www.personalchemistry.com/products/smith_vials.xml) the vessels include a sealing metal cap that typically holds a septum in place over the mouth of the vessel. These vessels and caps will typically remain intact and maintain their seal at pressures of about twenty atmospheres or even more. They cannot, however, release intermediate pressures. Additionally, because their functional status is either pressure-sealed or fully unsealed, they typically can not or should not be opened immediately upon completion of a pressure-generating reaction. As a result, the pressure-containing vessels must either be opened in some more sophisticated fashion, or be allowed to cool sufficiently to moderate the internal pressure.

As another consideration, a number of reactions can be or should be carried out at slightly elevated pressures, or will generate slightly elevated pressures as they proceed. In such cases, the amount of pressure generated needs to be both monitored and controlled; i.e., if the increased pressure is within a desired or expected limit, the reaction should be allowed to proceed. If, however, for some reason the pressure exceeds a predetermined or desired limit, the reaction may need to be slowed or stopped, and the excess pressure may need to be released for safety purposes.

Accordingly, in addition to measuring pressure without penetrating the vessel, a corresponding need exists for sealing a vessel in a manner that permits it to accommodate a desired higher pressure, while still providing a means for handling excess pressure in a safe and reliable fashion.

SUMMARY OF INVENTION

In a first aspect, the invention is a pressure-sealing, pressure-monitoring closure assembly for non-invasively sealing a reaction vessel to a defined release pressure in microwave-assisted chemistry. The closure comprises a pressure-resistant, microwave-transparent reaction vessel, one portion of which defines a mouth for the vessel, a flexible pressure-transmitting releasable cover assembly on the mouth of the vessel, a pressure transducer on the cover assembly and external to the vessel for monitoring the pressure in the vessel as exerted against the flexible cover assembly, and a clamp for urging the vessel, the cover assembly and the transducer together under a defined force so that when the pressure in the vessel exceeds the defined force, the cover assembly can flex and release the pressure from the vessel.

In another aspect the invention is a method for non-invasively monitoring and releasing pressure in a reaction vessel in microwave-assisted chemistry by clamping a microwave-transparent reaction vessel and a pressure-sensing transducer together with the transducer and the vessel in pressure-transmitting contact with one another, taring the clamping force from the transducer's measurement so that the transducer measures the net force exerted by pressure in the vessel and against the cover, applying microwave radiation to the vessel and its contents, and monitoring the pressure sensed by the transducer as the microwaves are applied to the vessel, characterized by clamping a flexible cover assembly to the vessel and adjusting the clamping force to a predetermined applied amount so that when pressure in the vessel exceeds the predetermined applied amount, the cover will flex and release the excessive pressure.

In another aspect, the invention is a method of noninvasive pressure measurement and control in microwave assisted chemistry comprising urging a transducer against a flexible, pressure-releasing portion of a microwave-transparent reaction vessel, using the transducer to measure the initial force with which the transducer is urged against the vessel, applying microwave radiation to the vessel and its contents to initiate or promote a chemical reaction therein, monitoring any increased force exerted by the vessel against the transducer as the chemical reaction proceeds, moderating the applied microwave radiation based upon the difference between the initial urging force and the increased force, and releasing any excess pressure through the pressure-releasing portion.

In another aspect, the invention is an instrument for microwave-assisted chemistry comprising a source of microwave radiation, a cavity in wave communication with the source, a vessel holder associated with the cavity for holding a reaction vessel in the cavity for exposure to microwaves from the source, a vessel clamp for engaging portions of the cavity and a reaction vessel when a vessel is in the vessel holder, a transducer in the clamp for bearing against a vessel in the vessel holder when the clamp engages the cavity with a vessel therein.

DETAILED DESCRIPTION

Figure 1:
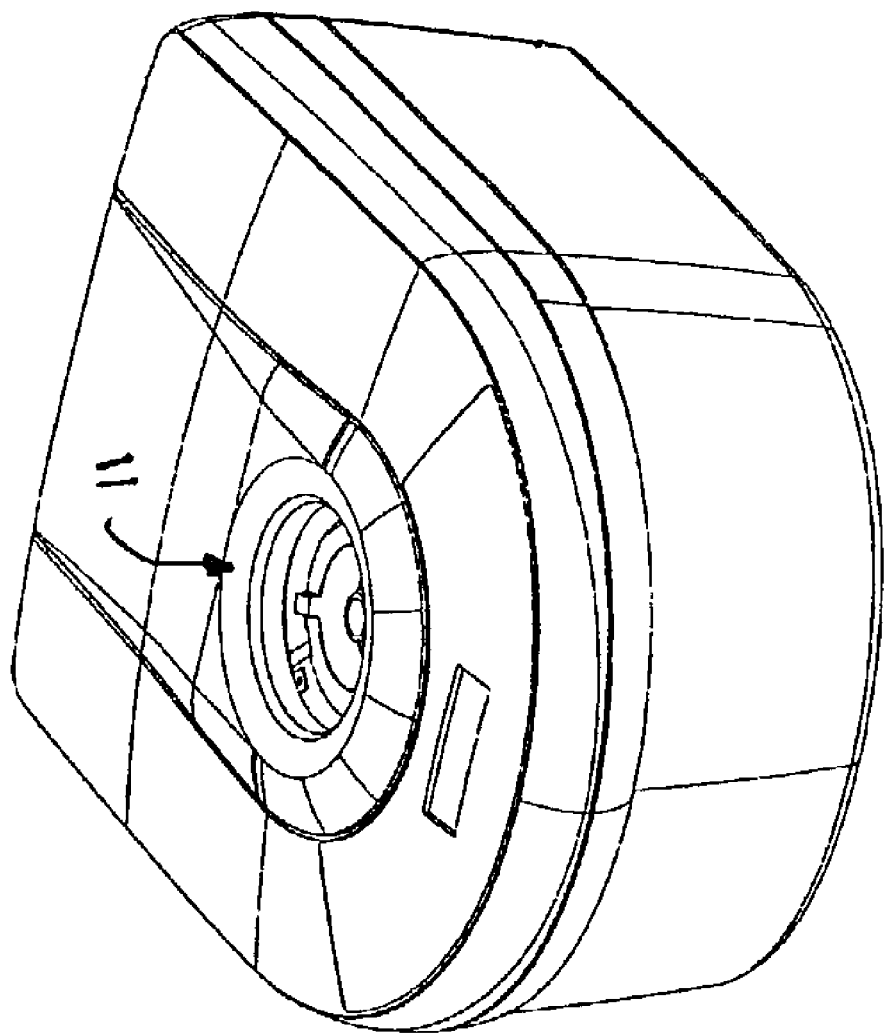
FIG. 1 is a perspective view of an instrument that can incorporate the pressure-releasing closure according to the present invention.

In a first aspect, the invention is a pressure-sealing, pressure-monitoring closure for non-invasively sealing a reaction vessel to a defined release pressure in microwave-assisted chemistry. FIG. 1 is a perspective view of a single mode microwave instrument broadly designated at 10. A microwave attenuator 11 covers a microwave cavity inside the instrument 10 and supports a reaction vessel 12 in a manner that is illustrated in more detail in FIG. 3. The closure of the present invention is used in conjunction with the attenuator 11 and a reaction vessel 12. The DISCOVER™ instrument from CEM Corporation, the assignee of the present invention, is exemplary (but not limiting) of the type of microwave instrument with which the present invention can be used.

Figure 2:
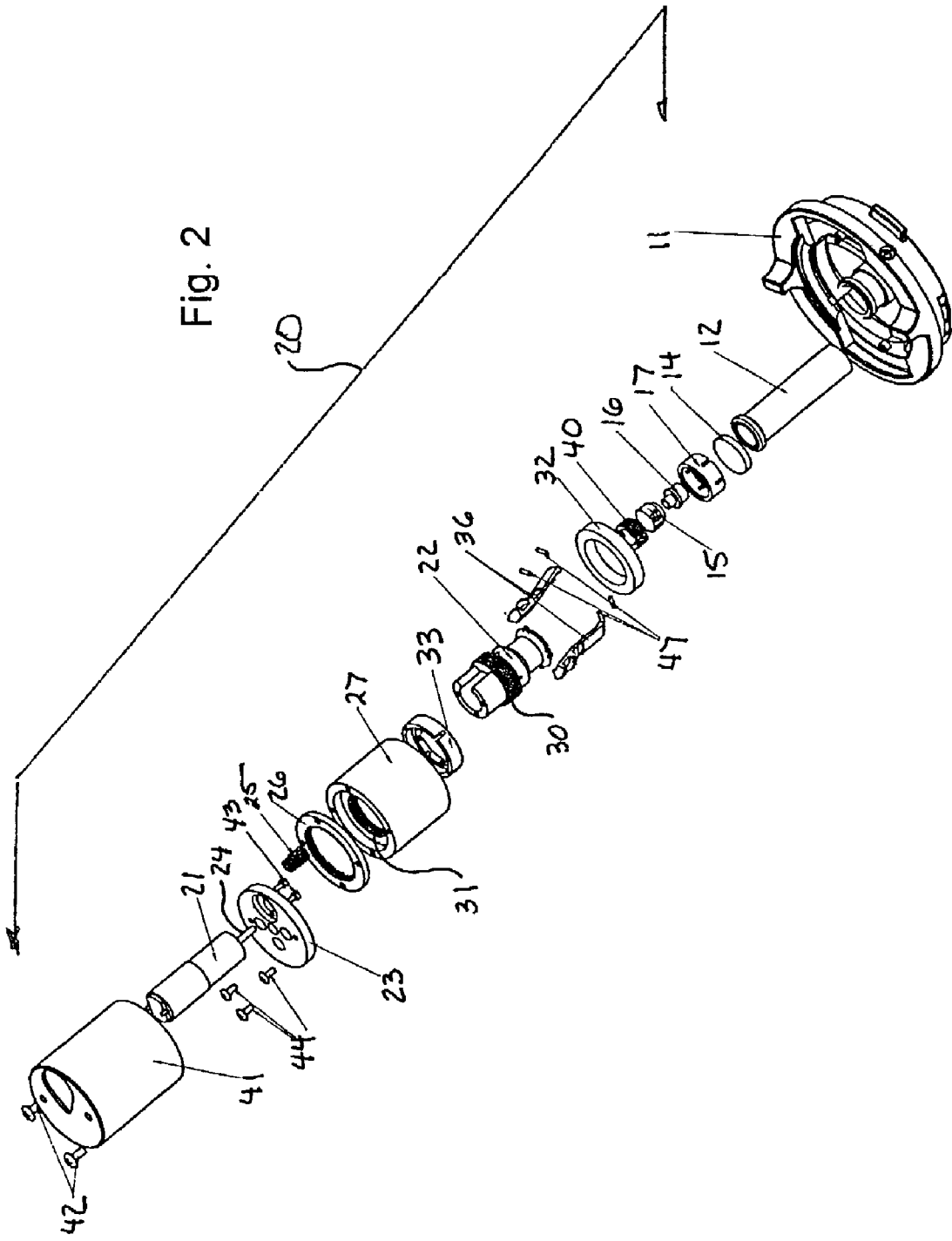
FIG. 2 is an exploded view of the pressure-releasing closure according to the present invention.

FIG. 2 is an exploded view of a closure according to the present invention. The closure incorporates a pressure-resistant, microwave-transparent reaction vessel 12, one portion of which defines a mouth 13 for the vessel 12. The vessel 12 can be formed of any material that provides the necessary transparency to microwave radiation, thermal stability, strength to contain expected pressure, and resistance to chemical attack from the materials placed in it, including reactants, products and by-products. In many circumstances, the reaction vessel 12 is formed of a material selected from the group consisting of glass, quartz and polymers, because these supply the desired properties.

A flexible pressure-transmitting releasable septum 14 is on the mouth 13 of the vessel 12. As used herein, the term "flexible" refers to a septum that can flex sufficiently under pressure (i.e., the internal gas pressure often generated in the vessel 12) to transmit the force of the pressure as it flexes.

A pressure transducer 15 is on the septum 14 and external to the vessel 12 for monitoring the pressure in the vessel 12 as exerted against the flexible septum 14. In the illustrated embodiment, the transducer 15 includes a transducer button 16 immediately adjacent the septum 14. In such an arrangement, the button 16 physically transmits force directly to the transducer 15 while insulating the transducer 15 from excess heat generated by a reaction in said vessel 12 and while protecting the transducer 15 from direct chemical contact with the contents of the vessel 12 if the septum 14 flexes sufficiently to open the vessel.

A clamp, designated by the lines 20, is described herein in terms of its component parts. The clamp 20 urges the vessel 12, the septum 14 and the transducer 15 together under a defined force so that when the pressure in the vessel 12 exceeds the defined force, the septum 14 can flex and release the pressure from the vessel 12.

The invention also includes a flexible cap 17 for maintaining the septum 14 on the mouth 13 of the vessel 12 in a gas-tight relationship independent of the clamp 20 and without interfering with the clamp 20 when the clamp 20 urges the vessel 12, the septum 14 and the transducer 15 together. In the illustrated embodiment, the cap 17 and septum 14 define a cover assembly that fixes the perimeter of the septum 14 to a shoulder or rim on the perimeter of the mouth 13 while leaving the transducer 15 or the button 16 in contact with the septum 14. The flexible cap 17 can serve at least two purposes. First, it helps maintain the septum 14 in a favorable position on the mouth 13 of the vessel 12. Second, it provides a releasable gas tight seal (although not necessarily a high-pressure seal) for the reaction vessel 12. Thus, for reactions that should avoid certain gases (e.g., oxygen) or that should include others, the cap 17 and septum 14 provide a means for including and maintaining such gases in the vessel 12 before, during, or after exposure to microwaves.

FIG. 2 further illustrates that the clamp 20 includes means for adjusting the force with which the clamp 20 urges the vessel 12, the transducer 15, the septum 14 and the flexible cap 17 together to thereby define the pressure at which cap 17 and septum 14 can flex and release pressure from the vessel 12. In the illustrated embodiment, the adjusting means comprises the motor 21 and a ram 22 in force-transmitting relationship with the transducer 15 and incrementally driven by the motor 21 for adjustably and incrementally changing the force with which the transducer 15 is clamped to the vessel 12.

Stated differently, in the absence of any clamping force, excess pressure (i.e., above atmospheric) inside the vessel 12 will simply push off the septum 14. With the flexible cap 17 in place, the pressure inside the vessel will be maintained until it exceeds either the flex resistance of the cover 14 or the flexing strength of the cap 17. With the clamp 20 in place, however, the pressure inside the vessel will be maintained until it reaches the predetermined force exerted by the clamp 20.

In preferred embodiments, the septum 14 is formed of a material such as butyl rubber, siloxane polymers, or equivalent materials. The septum 14 is not limited to such materials, however, and can be formed of other materials (e.g., metal) provided that it transmits pressure in predictable fashion and is otherwise suitable for use with the various reactants, products, and by-products with which it comes in contact.

Figure 3:
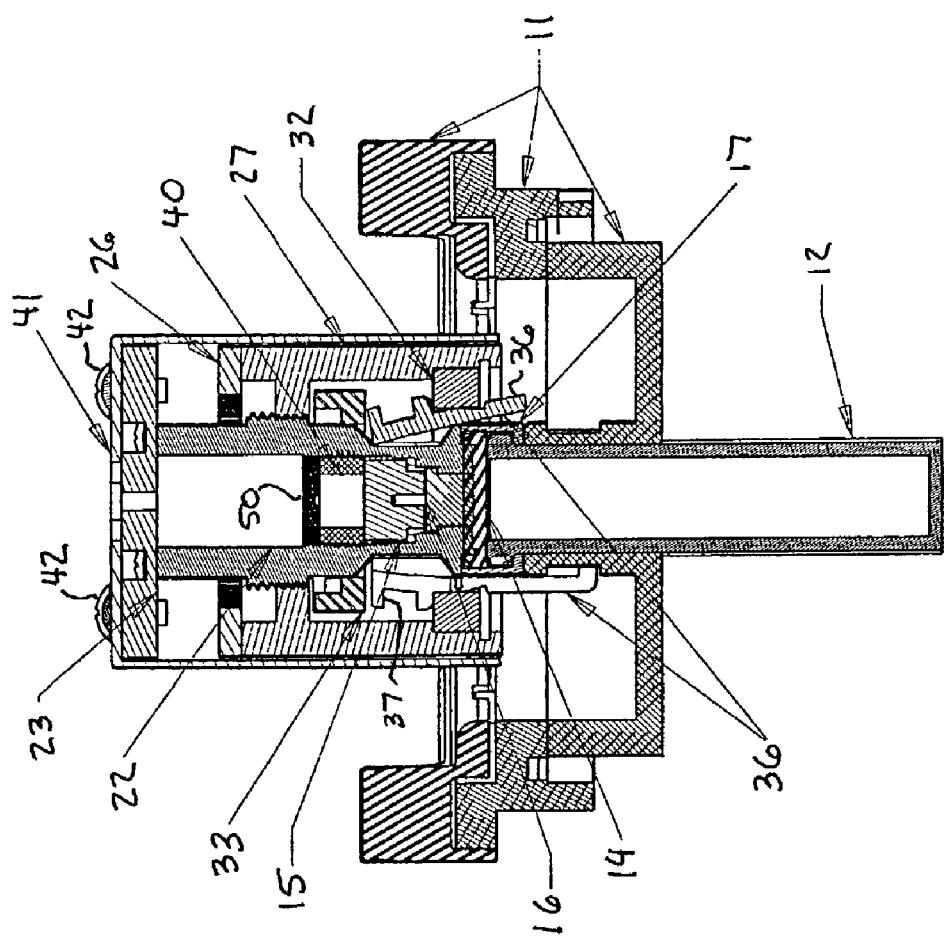
FIG. 3 is a cross-sectional view of the closure according to the present invention.
Figure 4:
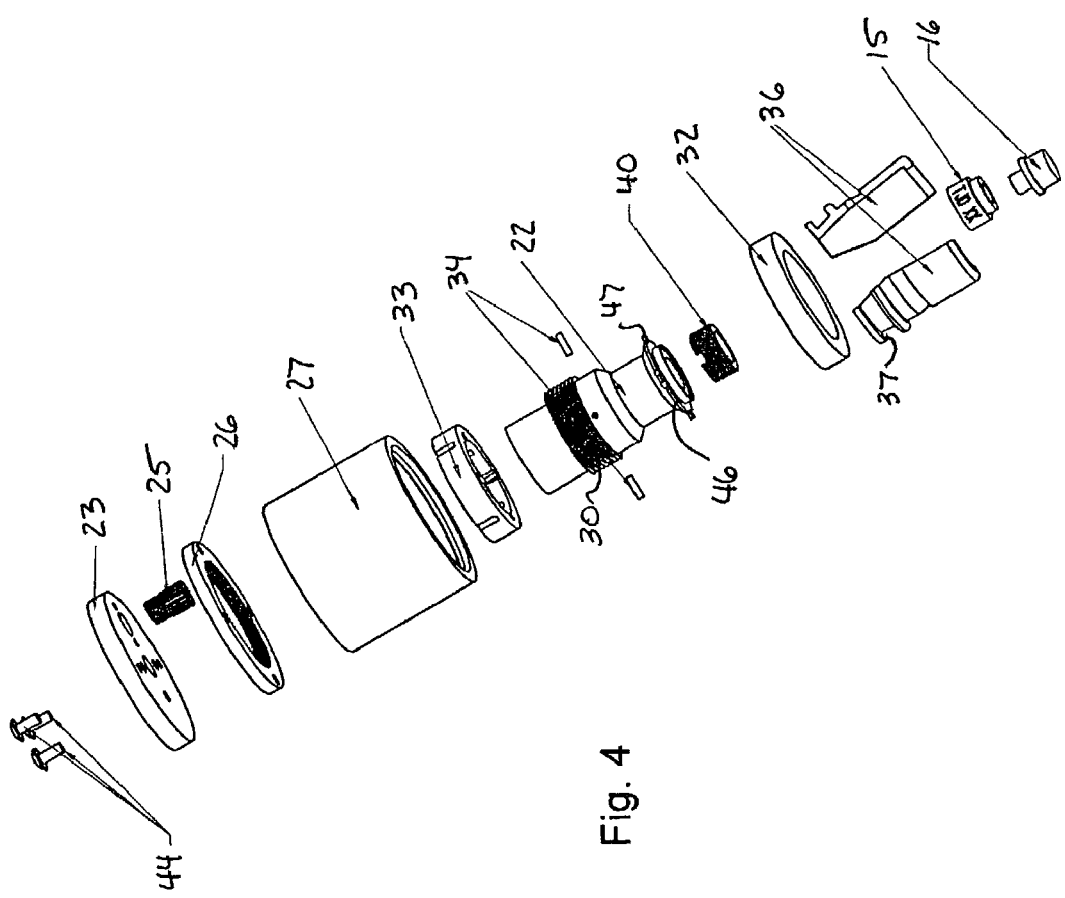
FIG. 4 is an enlarged view of a portion of the closure.

FIGS. 2, 3 and 4 illustrate the matter in which the preferred embodiment carries out the clamping according to the present invention. In the illustrated embodiment, the motor 21 is fixed to the motor mount 23. The motor shaft 24 carries a pinion gear 25. When the motor 21 rotates its shaft 24, the attached pinion gear 25 drives an internal gear 26 which is fixed to the body 27. In turn, the body 27 is fixed to the ram 22 by the engagement of between the threads 30 on the ram and the threads 31 on the interior of the body. Accordingly, when the motor rotates the pinion gear 25, the internal gear 26, the body 27, and the ram 22 move upwardly and downwardly to clamp or unclamp the transducer 15 against the septum 14 and cap 17 of the vessel 12. Only a very slight movement is required to apply the desired pressure, and in the illustrated embodiment, the total vertical movement of the ram is on the order of about 0.2 inches. The body 27 rotates against the bearing 32 at its lower (closest to the vessel 12) position, and is limited in its upward movement by the spacer 33 which provides a hard stop for the upward movement of the ram 22 in conjunction with the locking pins 34 (FIG. 4) that engage the slots 35 in the spacer 33.

The clamp 20 grips the attenuator 11 with the gripping fingers 36 two of which (out of a total of four in the preferred embodiment) are illustrated in FIGS. 2 and 4. A collar spring (not shown) holds the gripper fingers 36 in place by resting in the spring channel 37.

FIG. 2 also illustrates that the transducer 15 can desirably be positioned using a transducer holder 40. As additional items, FIG. 2 illustrates the cover 41 along with a pair of cover screws 42, motor mounting screws 43, and the additional mounting hardware 44.

A number of these same elements are shown in greater detail and larger size in FIG. 4 which illustrates the hardware inside of the cover 41. Thus, it will be understood that the motor 21 extends upwardly above the cover 41 in the illustrated embodiment and does not appear in FIG. 3 or FIG. 4. FIG. 4 also illustrates that the ram 22 carries a small collar 46 at its lower portions which in turn carries a series of small pins 47 that segregate the gripper fingers 36 from one another in the assembled clamp 20.

FIG. 3 illustrates a number of the same components in an assembled cross sectional view. In particular, FIG. 3 illustrates how the gripper fingers 36 engage those portions of the attenuator 11 that surround the reaction vessel 12. For the sake of comparison, the gripper finger 36 on the left hand side of the vessel 12 is shown in its engaged position with the attenuator 11, while the gripper finger 36 on the right hand side of the vessel 12 is shown in a released position. It will be understood that this is for purposes of illustration, and that the fingers would not be released and unreleased at the same time. As in the previous illustrations, the collar spring that holds the gripper fingers 36 is not illustrated, but the spring channel 37 in to which the spring fits is readily evident. FIG. 3 also illustrates the ram 22 in direct threaded engagement with the body 27, with lower portions of the body 27 resting against the bearing 32. The ram 22 includes a horizontal plate 50 that bears against the transducer holder 40 which in turn bears against the transducer 15 and the transducer button 16. These all in turn bear against the septum 14 and cap 17 on the vessel 12 in the manner described previously. Although the pinion gear 25 is not illustrated in FIG. 3, the internal gear 26 as fixed to the body 27 is illustrated and shows that as the internal gear 26 and the body 27 are driven by the motor 21, the body 27 will move upwardly and downwardly with respect to the ram 22 thus bringing the ram to bear against the transducer 15, the septum 14 and the cap 17. FIG. 3 also illustrates the vessel cap 17 that provides a gas tight seal for the vessel 12 independent of the clamping action of the remainder of the instrument and the closure.

The invention is not, however, limited to these particular mechanical arrangements, and other equivalent arrangements that provide the equivalent clamping function can be designed by those of ordinary skill in this art and without undue experimentation.

Figure 5:
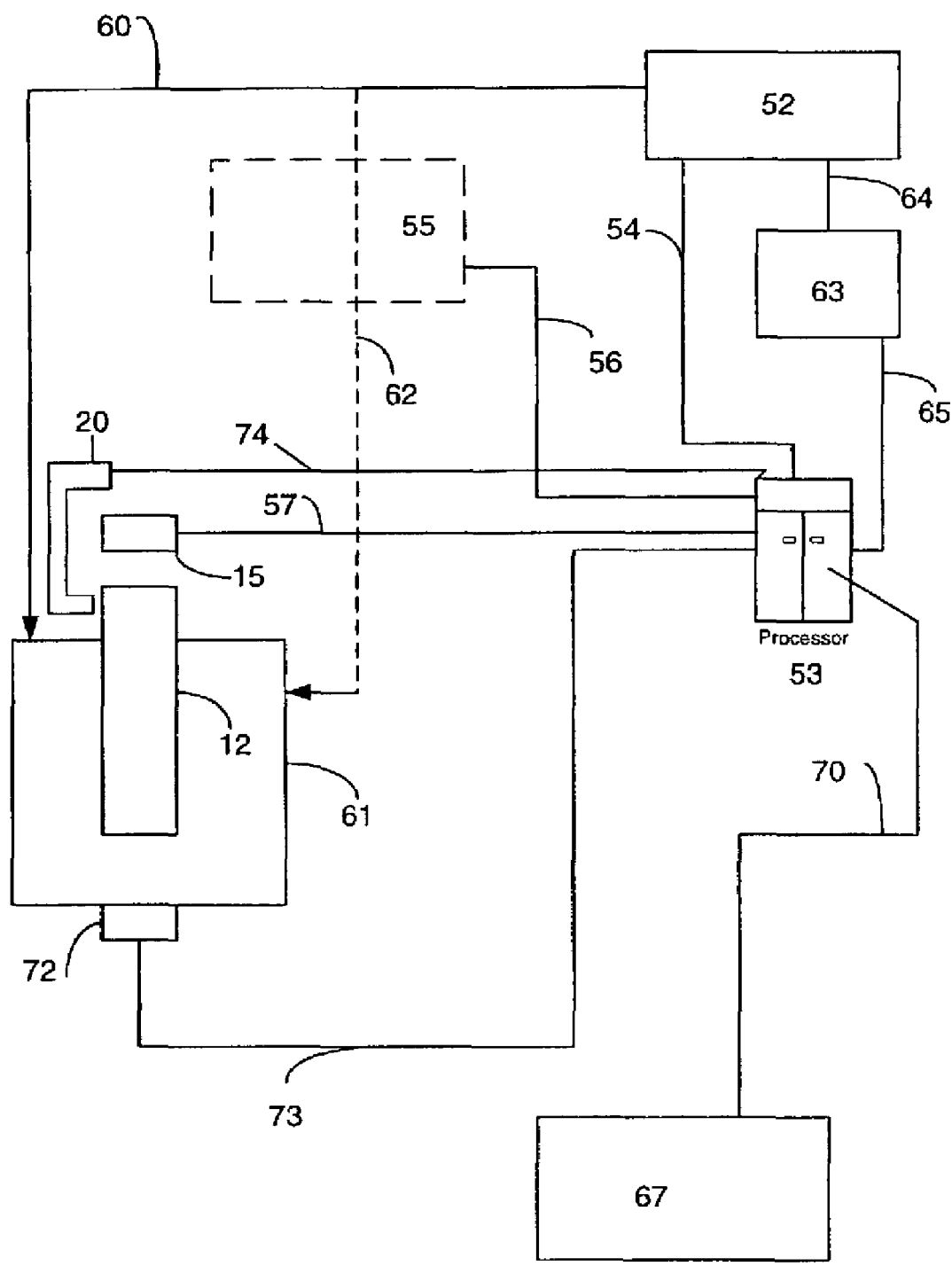
FIG. 5 is a schematic diagram of an instrument for microwave-assisted chemistry that incorporates the present invention.

FIG. 5 is a schematic diagram illustrating a number of additional elements and processes according to the claimed invention. FIG. 5 includes a microwave source 52 for applying microwave radiation to the vessel 12 in a cavity 61 that is in wave communication with the source 52, typically through the waveguide 60. The diagram also illustrates means (one version of which is illustrated at 55) for moderating the microwave radiation applied to the vessel 12. A processor 53 is in signal communication with: the source 52 through the connection 54; the moderating means 55 through the connection 56; and the transducer 15 through the connection 57. The processor and its connections provide the means for moderating the microwaves applied by the source 52 in response to pressure in the vessel 12 as measured by the transducer 15. FIG. 5 schematically illustrates one type of moderating means as the optical or wave-based moderating means 55 which changes the characteristics or focusing of the microwaves as they proceed from the source 52, typically through the waveguide indicated by the connecting line 60, into the cavity schematically illustrated at 61. The nature, design, and operation of waveguides is well-understood in this art and will not be otherwise described in detail The dashed arrow 62 indicates an alternative path for the waveguide which incorporates the optical moderating means 55 rather than a different moderating means. The optical moderation of microwaves can be carried out in a number of different manners depending upon the wavelength and power of the applied microwaves. An exemplary method of moderating microwaves in an optical manner is set forth in commonly assigned U.S. Pat. No. 5,796,080. Microwaves are, of course, outside of the range of frequencies visible to the human eye. Thus, the term "optical" is used herein to describe moderation of microwave radiation after it has been generated at a source.

The clamp 20 is also schematically illustrated in FIG. 5, and as described earlier, engages portions of the cavity 61 (typically through the attenuator; e.g., FIG. 3), and the reaction vessel 12 when a vessel is in the cavity (or the relevant vessel-holding portion of the cavity). In this manner, the transducer 15 in the clamp 20 bears against the vessel 12 in the cavity 61 when the clamp engages the cavity, or its attenuator (e.g., FIGS. 2–4).

The clamp 20 is also in communication with the processor 53 through the respective connection 74 thus permitting the transducer 15 to measure the net pressure from the vessel 12 rather than the gross pressure applied by the clamp 20. Just as advantageously, the communication between the clamp 20 and the processor 53 provides the means for adjusting the force with which the clamp 20 engages the transducer 15 against the vessel 12. The input/output 67, and its communication with the processor 53, also facilitates this adjustment.

FIG. 5 also schematically illustrates a power supply 63, and it is well understood that the microwaves can be moderated by changing the power applied to a microwave source. Accordingly, the power supply 63 and source 52 are in communication through the connection 64 and the power supply 63 is in signal communication with the processor 53 through the connection 65. Because the processor 53 is in signal communication to the source 52, the application of microwaves can also be moderated by changing the duty cycle of the source. The moderation of the duty cycle is a well understood and generally conventional manner of moderating microwaves and thus has the advantages of simplicity. As understood by those in the art, however, controlling the power can have a more sophisticated effect for changing the microwaves in incremental fashion. A method and apparatus for doing this in connection with microwave-assisted chemistry are set forth in commonly assigned U.S. Pat. No. 6,084,226 which is incorporated entirely herein by reference.

The connections between elements referred to herein and illustrated in FIG. 5 are typically electrical connections, most commonly wires and connectors. The invention is not limited to electrical wiring, however, and other signal connections such as fiber optics or even wireless connections can be used as desired, necessary or appropriate.

In its method aspects, the invention represents in improvement for non-invasively monitoring and releasing pressure in a reaction vessel in microwave-assisted chemistry. In this aspect, the invention comprises clamping a microwave-transparent reaction vessel 12, and a pressure-sensing transducer 15 together with the transducer 15 and the vessel's flexible, pressure-releasing cover assembly (e.g., cap 17 and septum 14) in pressure-transmitting contact with one another, taring the clamping force from the transducer's measurement so that the transducer 15 measures the net force exerted by pressure in the vessel 12 and against the cover assembly, applying microwave radiation to the vessel 12 and its contents, and monitoring the pressure sensed by the transducer 15 as the microwaves are applied to the vessel; i.e., as the reaction proceeds. Although the term "clamping" is used herein, it is used in a broad sense to include synonyms such as fastening, holding, gripping or grasping.

In preferred embodiments, the clamping step comprises clamping the flexible cap 17 and septum 14 to the vessel 12 and adjusting the clamping force to a predetermined applied amount so that when pressure in the vessel 12 exceeds the predetermined applied amount, the cap 17 and septum 14 will flex and release the excessive pressure. In this manner, the instrument and closure can be used to set the pressure at which the closure will release, and this pressure can be selected (within the physical strength limits of the various elements) as desired based upon the reaction being carried out or other relevant factors.

Just as importantly, however, the described structure permits the pressure in the vessel 12 to be monitored at pressures below the predetermined release pressure, and in turn the microwave radiation applied to the vessel 12 can be moderated in response to the measured pressure. In this manner the progress of a reaction can be controlled as desired or necessary under various circumstances.

In a preferred embodiment, the step of moderating the microwave radiation comprises programming the processor 53 that is in signal communication with the microwave source 52 applying the radiation and in signal communication with the transducer 15.

As general considerations, the method can also include the steps of adding reactants to the vessel 12, placing the septum on the vessel 12, and sealing the septum 14 to the vessel 12 with the flexible cap 17, all prior to the step of clamping the vessel 12, the cap 17, the septum 14, and the transducer 15 together.

The method can further comprise the step of stopping the applied microwaves, allowing the vessel 12 to cool, and then unclamping the vessel 12 to release any residual pressure.

With the processor 53 and its relationship to the other elements understood, the method can further comprise the steps of recording the initial clamping force as measured by the transducer 15 prior to applying the microwave radiation, then ignoring the initial force when measuring the pressure with the transducer 15 as the microwaves are being applied.

By ignoring the initial force in a manner entirely analogous to taring a balance the force (pressure) measured thereafter represents the pressure generated inside of the vessel 12.

In this aspect, the step of taring the clamping force can comprise programming the transducer 15 to ignore the initial clamping force prior to the step of applying the microwave radiation, and the step of programming the transducer 15 essentially comprises programming the processor 53 that is in signal communication with the transducer 15 as illustrated in FIG. 5.

Expressed in another aspect, the method of non-invasive pressure measurement and control in microwave assisted chemistry according to the invention includes the steps of urging the transducer 15 against the flexible portion of a microwave transparent reaction vessel 12, using the transducer 15 to measure the initial force with which the transducer is urged against the vessel 12, applying microwave radiation to the vessel 12 and its contents to initiate or promote a chemical reaction therein, monitoring any increased force exerted by the vessel 12 against the transducer 15 as the chemical reaction proceeds, and potentially moderating the applied microwave radiation based upon the difference between the initial urging force and the increased force.

As set forth, earlier, in preferred embodiments, the step of urging the transducer 15 against the vessel 12 comprises urging the transducer 15 in contact against the flexible cover assembly on the mouth 13 of the vessel 12.

In preferred embodiments, the step of measuring the initial force comprises sending a signal from the transducer 15 to the processor 53 in communication with the transducer 15 and from the processor 53 to the input/output 67 in communication with the processor 53 through the connection 70.

In this embodiment, the step of monitoring the increased force likewise comprises forwarding a signal from the transducer 15 to the processor 53 in communication with the transducer 15. In preferred aspects, the invention comprises forwarding a pressure measurement signal in turn from the processor 53 to an output, again illustrated schematically as the input/output 67 in FIG. 5.

As used herein, the terms "processor," "input," and "output," have their well-understood meanings in the computer and electronic arts. Downing, Dictionary of Internet and Computer Terms, ($6^{th}$ ed. 1998), and the Microsoft Computer Dictionary, ($4^{th}$ ed. 1999), are exemplary sources for defining and understanding these terms.

Similarly, techniques for using measured information to control a process in a feedback fashion are generally well-understood in this and other arts. Exemplary techniques can be found in Dorf, The Electrical Engineering Handbook, 2d ed. 1997) at Chapter 100, "Control Systems." The microwave source 52 schematically illustrated in FIG. 5 can be any suitable source of microwave radiation, and is typically selected from the group consisting of magnetrons, klystrons, and solid state sources. Similarly, the cavity 61 comprises a single mode cavity in preferred embodiments for the reasons set forth in the background of the invention.

In preferred embodiments, the instrument also comprises means such as the infrared detector schematically illustrated at 72 for measuring the temperature in the cavity 61. Depending upon the focusing of the temperature detector 72 and other factors, it will be understood that the detector can measure the temperature of the environment in the cavity, the temperature of the vessel, or the temperature of the contents, or some combination of all of these factors. FIG. 5 also illustrates that the temperature detector 72 is in signal communication with the processor 53 through its connection 73. A detailed explanation of infra-red temperature control in the context of microwave assisted chemistry is set forth in commonly-assigned U.S. Pat. No. 6,227,041 the contents of which are incorporated entirely herein by reference.

Perhaps most advantageously, the structure set forth herein demonstrates how the force with which the clamp 20 engages the transducer 15 against the vessel 12 can be adjusted. This is typically carried out by the input/output means 67 and the processor 53 for programming the processor 53 to apply a predetermined engaging force to the clamp 20 and the transducer 15 against the vessel by controlling the motor 21 (FIG. 2).

Figure 6:
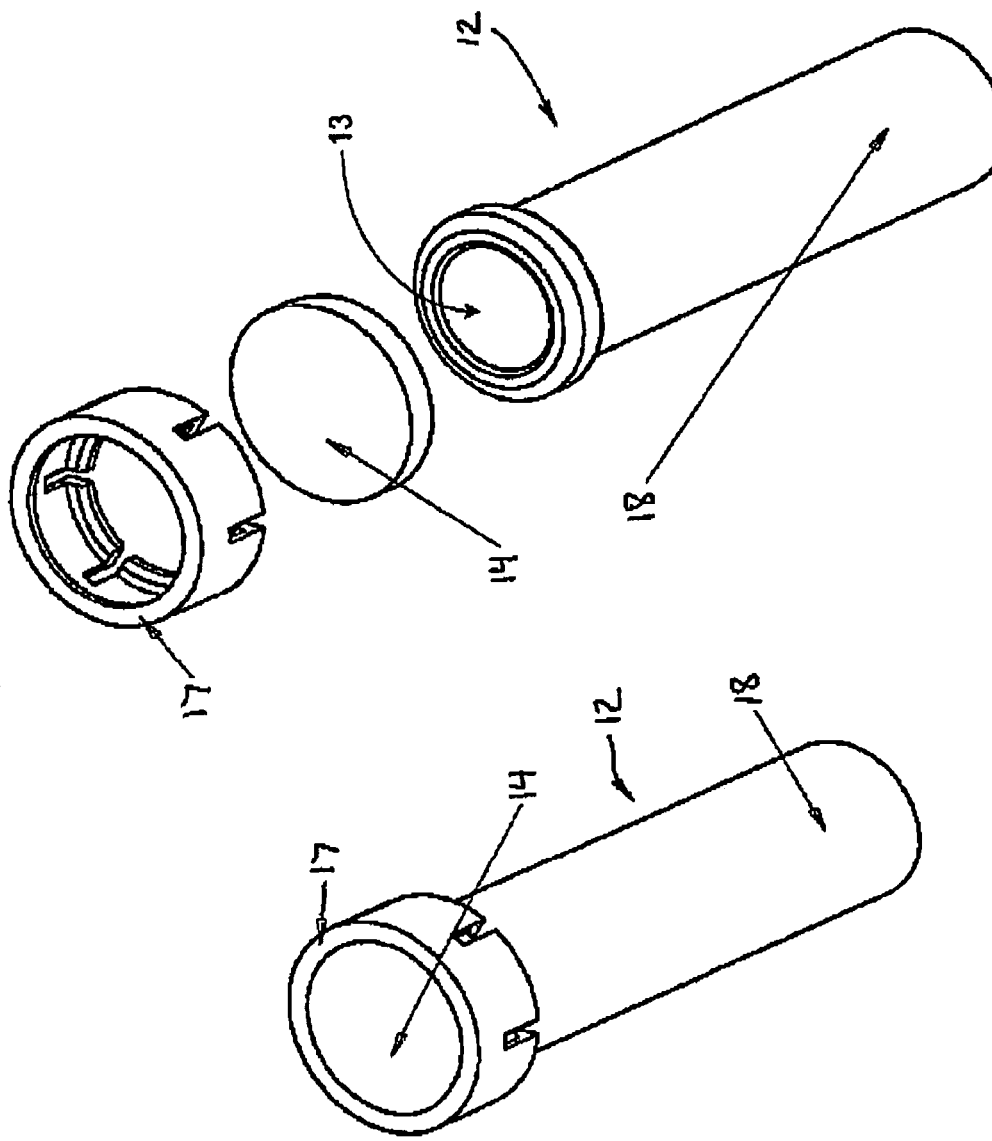
FIG. 6 is a perspective view of the vessel and its septum and cap in both assembled and exploded fashion.

FIG. 6 is an enlarged, side by side perspective view of the vessel 12, the septum 14, and the cap 17, and illustrates the vessel aspects of the present invention in both assembled and exploded fashion. The vessel 12 includes a microwave transparent well 18 illustrated as the lower portions of the vessel 12 in FIG. 6. As illustrated in FIG. 6, the vessel 12 is cylindrical in shape and resembles a test tube, which is a convenient shape for a number of reasons. It will be understood, however, by those of ordinary skill in this art that the shape of the vessel 12 or well 18 can vary, provided the vessel otherwise meets the criteria for being inert to the reactants, products and byproducts, substantially transparent to microwave radiation, and strong enough to withstand the expected pressures.

The exploded portion of FIG. 6 also illustrates the mouth 13 and shows how the flexible septum 14 is positioned on the mouth 13. In particular, FIG. 6 illustrates the flexible cap 17 in greatest detail. The cap 17 engages the mouth 13, particularly through the mouth's lip or shoulder 19, and secures the septum 14 in a pressure sealing relationship on the mouth 13 that is defined by the flexing strength of the cap 17 to thereby maintain the septum 14 in the pressure sealing relationship under pressures less than the flexing strength of the cap 17 and for permitting the cap 17 and septum 14 to flex and controllably release pressures in the vessel 12 that are greater than the flexing strength of the cap 17. In preferred embodiments and for typical reaction purposes, the cap 17 has a flexing strength of at least one atmosphere, and more preferably a flexing strength of at least two atmospheres.

It will also be understood that the term "releasing pressure" in reality, refers to the release of a gas from the vessel 12 that exerts pressure against the interior of the vessel. This is a basic understanding, however, and need not be carried forward in any further detail.

FIG. 6 illustrates the cap 17 and the septum 14 as separate pieces, but in other embodiments, they can be formed as an integral piece, as may be more convenient under certain circumstances. The use of separate pieces can help optimize the specific performance parameters of the septum 14 and those of the cap 17, while the use of a single integral piece can offer manufacturing or handling advantages based upon a fewer number of parts.

In presently preferred embodiments, the cap is typically formed of a polymer, most preferably polypropylene, and the septum is typically formed from butyl rubber or a siloxane polymer, either of which is chosen as may be appropriate for its flexing strength and general lack of reactivity with most other chemical reactants. The choice of these materials is not limited to polypropylene, butyl rubber and siloxane, and it will be understood that any materials that provide appropriate flexing and pressure release characteristics can be successfully incorporated.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A pressure-sealing, pressure-monitoring closure for non-invasively sealing a reaction vessel to a defined release pressure in microwave-assisted chemistry, said closure comprising:
   a pressure-resistant, microwave-transparent reaction vessel, one portion of which defines a mouth for said vessel;
   a flexible pressure-transmitting septum on said mouth of said vessel;
   a flexible cap for fixing the perimeter of said septum to the perimeter of said mouth of said vessel in an independent gas-tight relationship;
   a pressure transducer contacting said septum and external to said vessel for monitoring the pressure in said vessel as exerted against said flexible septum; and
   an adjustable a clamp for urging said vessel, said septum, said cap, and said transducer together under a defined force so that when the pressure in said vessel exceeds both the defined clamping force and the gas-tight relationship of said cap and said septum, said septum and said cap can flex and release the pressure from said vessel.

2. A closure according to claim 1 and further comprising:
   a microwave source for applying microwave radiation to said vessel and its contents; means for moderating the microwave radiation applied to the vessel; and
   a processor in signal communication with said source, said moderating means and said transducer for moderating the microwaves applied by said source in response to the pressure in said vessel as measured by said transducer.

3. A closure according to claim 2 wherein said microwave moderating means comprises means for changing the power of said microwave source.

4. A closure according to claim 2 wherein said microwave moderating means comprises means for changing the duty cycle of the source.

5. A closure according to claim 1 wherein said clamp includes means for adjusting the force with which the clamp urges said vessel, said transducer and said cover together to thereby define the pressure at which said cover can flex and release pressure from said vessel.

6. A closure according to claim 1 wherein said transducer includes a transducer button immediately adjacent said cover assembly for insulating said transducer from excess heat generated by a reaction in said vessel and for protecting said transducer from direct chemical contact with the contents of said vessel if said cover assembly flexes sufficiently to open said vessel.

7. A closure according to claim 1 wherein said reaction vessel is formed of a material selected from the group consisting of glass, quartz and polymers.

8. A closure according to claim 1 wherein said septum is selected from the group consisting of rubbers and polymers and said flexible cap is polymeric.

9. A closure according to claim 8 wherein said septum is selected from the group consisting of butyl rubbers and siloxane polymers and said cap comprises polypropylene.

10. A pressure-sealing, pressure-monitoring closure for non-invasively sealing a reaction vessel to a defined release pressure in microwave-assisted chemistry, said closure comprising:
    a pressure-resistant, microwave-transparent reaction vessel, one portion of which defines a mouth for said vessel;
    a flexible pressure-transmitting releasable cover assembly on said mouth of said vessel;
    a pressure transducer on said cover assembly and external to said vessel for monitoring the pressure in said vessel as exerted against said flexible cover assembly; and
    an adjustable clamp for urging said vessel, said cover assembly and said transducer together under a defined force so that when the pressure in said vessel exceeds the defined force said cover assembly can flex and release the pressure from said vessel; said clamp including
    a motor; and
    a ram in force-transmitting relationship with said transducer and incrementally driven by said motor for adjustably and incrementally changing the force with which said transducer is clamped to said cover.

11. A method for non-invasively monitoring and releasing pressure in a reaction vessel in microwave-assisted chemistry, the method comprising:
    clamping a microwave-transparent reaction vessel and a pressure-sensing transducer together with the transducer and the vessel cover in adjustable pressure-transmitting contact with one another;
    taring the clamping force from the transducer's measurement so that the transducer measures the net force exerted by pressure in the vessel and against the cover;
    applying microwave radiation to the vessel and its contents; and
    monitoring the pressure sensed by the transducer as the microwaves are applied to the vessel;
    characterized in that:
    the clamping step comprises clamping a flexible cover assembly to the vessel and adjusting the clamping force to a predetermined applied amount so that when pressure in the vessel exceeds the predetermined applied amount, the cover will flex and release the excessive pressure.

12. A method of microwave-assisted chemistry according to claim 11 comprising the steps of:
    adding reactants to the vessel;
    placing the cover on the vessel; and
    sealing the cover to the vessel with a gas-tight seal;
    all prior to the step of clamping the vessel, the cover and the transducer together.

13. A method of microwave-assisted chemistry according to claim 11 comprising the steps of:
    stopping the applied microwaves;
    allowing the vessel to cool; and
    unclamping the vessel to release any residual pressure.

14. A method of microwave-assisted chemistry according to claim 11 and further comprising moderating the microwave radiation applied to the vessel in response to the measured pressure.

15. A method of microwave-assisted chemistry according to claim 14 wherein the step of moderating the microwave radiation comprises programming a processor that is in signal communication with the microwave source applying the radiation and in signal communication with the transducer.

16. A method of microwave-assisted chemistry according to claim 11 wherein the step of taring the clamping force comprises:
  recording the initial clamping force as measured by the transducer prior to applying the microwave radiation; and
  ignoring the initial force when measuring the pressure with the transducer as the microwaves are being applied.

17. A method of microwave-assisted chemistry according to claim 11 wherein the step of taring the clamping force comprises programming the transducer to ignore the initial clamping force prior to the step of applying the microwave radiation.

18. A method of microwave-assisted chemistry according to claim 17 wherein the step of programming the transducer comprises programming a processor that is in signal communication with said transducer.

19. A method of noninvasive pressure measurement and control in microwave assisted chemistry, the method comprising:
  adjustably urging a transducer against a flexible, pressure-releasing portion of a microwave-transparent reaction vessel;
  using the transducer to measure the initial force with which the transducer is urged against the vessel;
  applying microwave radiation to the vessel and its contents to initiate or promote a chemical reaction therein;
  monitoring any increased force exerted by the vessel against the transducer as the chemical reaction proceeds;
  moderating the applied microwave radiation based upon the difference between the initial urging force and the increased force; and
  releasing any excess pressure through the pressure-releasing portion.

20. A pressure measurement method according to claim 19 wherein the step of urging the transducer against the vessel comprises urging the transducer in contact against a flexible cover assembly on the mouth of the vessel.

21. A pressure measurement method according to claim 19 wherein the step of measuring the initial force comprises sending a signal from the transducer to a processor in communication with the transducer and from the processor to an output in communication with the processor.

22. A pressure measurement method according to claim 19 wherein the step of applying microwave radiation comprises applying the radiation from a source of microwave radiation.

23. A pressure measurement method according to claim 19 wherein the step of monitoring the increased force comprises forwarding a signal from the transducer to a processor in communication with the transducer.

24. A pressure measurement method according to claim 23 and further comprising forwarding a pressure-measurement signal from the processor to an output.

25. A pressure measurement method according to claim 19 wherein the step of moderating the microwave radiation comprises moderating the microwave power.

26. A pressure measurement method according to claim 19 wherein the step of moderating the microwave radiation comprises moderating the microwave duty cycle.

27. A pressure measurement method according to claim 19 wherein the step of moderating the microwave radiation comprises optically moderating the microwave radiation.

28. An instrument for microwave-assisted chemistry comprising:
  a source of microwave radiation;
  a cavity in wave communication with said source;
  a vessel holder associated with said cavity for holding a reaction vessel in said cavity for exposure to microwaves from said source;
  a flexible, pressure-releasing cover assembly for a reaction vessel;
  a vessel clamp for engaging portions of said cavity, said cover assembly and a reaction vessel when a vessel is in said vessel holder;
  a transducer in said clamp for bearing against a vessel in said vessel holder when said clamp engages said cavity with a vessel therein; and
  means for adjusting the transducer so that said transducer measures net pressure from the vessel rather than gross pressure applied by said vessel clamp.

29. An instrument according to claim 28 wherein said transducer adjusting means comprises:
  a processor in signal communication with said transducer;
  an input in communication with said processor; and
  an output in signal communication with said processor.

30. An instrument according to claim 28 wherein said vessel holder includes a microwave attenuator.

31. An instrument according to claim 30 wherein said clamp engages said attenuator.

32. An instrument according to claim 30 or 31 wherein said clamp engages aid vessel in said attenuator.

33. An instrument according to claim 28 and further comprising a processor in signal communication with said source and said transducer for moderating the microwaves from said source in response to pressure measurements from said transducer.

34. An instrument according to claim 33 and further comprising means for adjusting the force with which said clamp engages said transducer against a vessel.

35. An instrument according to claim 34 and further comprising input and output means to and from said processor for programming said processor to apply a predetermined engaging force to said clamp and said transducer against a vessel.

36. An instrument according to claim 28 wherein said microwave source is selected from the group consisting of magnetrons, klystrons and solid state sources.

37. An instrument according to claim 28 wherein said cavity comprises a single mode cavity.

38. An instrument according to claim 28 and further comprising a waveguide between said source and said cavity for directing microwaves from said source to said cavity.

39. An instrument according to claim 28 and further comprising means for measuring the temperature in said cavity.

40. An instrument according to claim 39 wherein said temperature measuring means is in signal communication with said processor for moderating the application of microwaves from said source in response to the measured temperature.

* * * * *

UNITED STATES PATENT AND TRADEMARK OFFICE
CERTIFICATE OF CORRECTION

| | | |
|---|---|---|
| PATENT NO. | : 7,144,739 B2 | Page 1 of 1 |
| APPLICATION NO. | : 10/065851 | |
| DATED | : December 5, 2006 | |
| INVENTOR(S) | : William E. Jennings | |

It is certified that error appears in the above-identified patent and that said Letters Patent is hereby corrected as shown below:

In claim 1, column 11, line 24, delete "an adjustable a clamp" and insert therefor -- "an adjustable clamp" --

Signed and Sealed this

Twentieth Day of February, 2007

JON W. DUDAS
*Director of the United States Patent and Trademark Office*